United States Patent
Thorman et al.

(10) Patent No.: US 8,258,359 B2
(45) Date of Patent: Sep. 4, 2012

(54) ALKYLATION OF TOLUENE TO FORM STYRENE AND ETHYLBENZENE

(75) Inventors: Joseph Thorman, Houston, TX (US); James Butler, Houston, TX (US); Sivadinarayana Chinta, Missouri City, TX (US)

(73) Assignee: Fina Technology, Inc., Houston, TX (US)

( * ) Notice: Subject to any disclaimer, the term of this patent is extended or adjusted under 35 U.S.C. 154(b) by 75 days.

(21) Appl. No.: 12/763,235

(22) Filed: Apr. 20, 2010

(65) Prior Publication Data

US 2011/0257451 A1    Oct. 20, 2011

(51) Int. Cl.
  *C07C 2/66* (2006.01)
(52) U.S. Cl. .......................... 585/435; 585/467; 585/469
(58) Field of Classification Search .................. 585/435, 585/467, 469
  See application file for complete search history.

(56) References Cited

U.S. PATENT DOCUMENTS

| 4,115,424 A | 9/1978 | Unland et al. |
| 4,140,726 A | 2/1979 | Unland et al. |
| 4,181,629 A | 1/1980 | Cairati et al. |
| 4,463,204 A * | 7/1984 | Liu .............................. 585/437 |
| 4,479,024 A | 10/1984 | Bruylants et al. |
| 2010/0041931 A1 | 2/2010 | Pelati et al. |

OTHER PUBLICATIONS

B. Kumari Vasanthy et al., Applied Catalysis A: General, vol. 138 (1996) p. 51-61.

* cited by examiner

*Primary Examiner* — Thuan Dinh Dang (57) ABSTRACT

A process is disclosed for making styrene and/or ethylbenzene by reacting toluene with a C1 source over a catalyst in one or more reactors to form a product stream comprising styrene and/or ethylbenzene where the catalyst time on stream prior to regeneration is less than 1 hour.

5 Claims, 5 Drawing Sheets

ALKYLATION OF TOLUENE TO FORM STYRENE AND ETHYLBENZENE

CROSS-REFERENCE TO RELATED APPLICATIONS

The present invention is related to co-pending application titled Method of Coupling a Carbon Source with Toluene to form Styrene and Ethylbenzene filed by Fina Technology, Inc. on the same date as this filing.

FIELD

The present invention relates to a method for the production of styrene and ethylbenzene. More specifically, the invention relates to the alkylation of toluene with methanol and/or formaldehyde to produce styrene and ethylbenzene.

BACKGROUND

Styrene is an important monomer used in the manufacture of many plastics. Styrene is commonly produced by making ethylbenzene, which is then dehydrogenated to produce styrene. Ethylbenzene is typically formed by one or more aromatic conversion processes involving the alkylation of benzene.

Aromatic conversion processes, which are typically carried out utilizing a molecular sieve type catalyst, are well known in the chemical processing industry. Such aromatic conversion processes include the alkylation of aromatic compounds such as benzene with ethylene to produce alkyl aromatics such as ethylbenzene. Typically an alkylation reactor, which can produce a mixture of monoalkyl and polyalkyl benzenes, will be coupled with a transalkylation reactor for the conversion of polyalkyl benzenes to monoalkyl benzenes. The transalkylation process is operated under conditions to cause disproportionation of the polyalkylated aromatic fraction, which can produce a product having an enhanced ethylbenzene content and reduced polyalkylated content. When both alkylation and transalkylation processes are used, two separate reactors, each with its own catalyst, can be employed for each of the processes.

Ethylene is obtained predominantly from the thermal cracking of hydrocarbons, such as ethane, propane, butane, or naphtha. Ethylene can also be produced and recovered from various refinery processes. Thermal cracking and separation technologies for the production of relatively pure ethylene can account for a significant portion of the total ethylbenzene production costs.

Benzene can be obtained from the hydrodealkylation of toluene that involves heating a mixture of toluene with excess hydrogen to elevated temperatures (for example 500° C. to 600° C.) in the presence of a catalyst. Under these conditions, toluene can undergo dealkylation according to the chemical equation: $C_6H_5CH_3+H_2 \rightarrow C_6H_6+CH_4$. This reaction requires energy input and as can be seen from the above equation, produces methane as a byproduct, which is typically separated and may used as heating fuel for the process.

Other known process include the alkylation of toluene to produce styrene and ethylbenzene. In this alkylation process, various aluminosilicate catalysts are utilized to react methanol and toluene to produce styrene and ethylbenzene. However, such processes have been characterized by having very low yields in addition to having very low selectivity to styrene and ethylbenzene.

In view of the above, it would be desirable to have a process of producing styrene and/or ethylbenzene that does not rely on thermal crackers and expensive separation technologies as a source of ethylene. It would further be desirable to avoid the process of converting toluene to benzene with its inherent expense and loss of a carbon atom to form methane. It would be desirable to produce styrene without the use of benzene and ethylene as feedstreams. It would also be desirable to produce styrene and/or ethylbenzene in one reactor without the need for separate reactors requiring additional separation steps. Furthermore, it is desirable to have a reactor system able to achieve a high yield and selectivity to styrene and ethylbenzene.

SUMMARY

An embodiment of the present invention is a process for making styrene and/or ethylbenzene by reacting toluene with a C1 source, such as formaldehyde, over a catalyst in one or more reactors having a catalyst time on stream prior to regeneration of less than 1 hour. Embodiments can have a catalyst time on stream prior to regeneration of less than 30 minutes, optionally less than 20 minutes, optionally less than 10 minutes, optionally less than 5 minutes, optionally less than 1 minute, optionally less than 30 seconds, optionally less than 10 seconds, optionally less than 5 seconds.

An embodiment of the present invention is a process for making styrene by converting a C1 source to formaldehyde and coupling the formaldehyde with toluene in one or more reactors having a catalyst time on stream prior to regeneration of less than 1 hour to form a product stream including styrene and/or ethylbenzene.

Another embodiment of the present invention is a process for making styrene by converting methanol to formaldehyde and coupling methanol and/or formaldehyde with toluene in one or more reactors having a catalyst time on stream prior to regeneration of less than 1 hour to form a product stream including styrene and/or ethylbenzene. The product stream can also include one or more of hydrogen, water, or methanol. The methanol, if any is present, can be separated from the product stream and then recycled to the one or more reactors.

The process may include utilizing one or more reactors including an oxidation reaction zone to convert methanol into formaldehyde and water. The process can optionally include utilizing one or more reactors including a dehydrogenation reaction zone to convert methanol into formaldehyde and hydrogen. The one or more reactors can also include a reaction zone under reaction conditions containing a catalyst for reacting toluene and formaldehyde to form styrene and ethylbenzene. The catalyst can be an acid, basic or neutral catalyst, and can be an acid, basic or neutral zeolite catalyst. The catalyst can be based on a zeolite selected from the group consisting of faujasites. The catalyst can include one or more promoters chosen from the group of alkali elements, alkaline earth elements, rare earth elements, Y, Zr, Nb, Co, Ga and B.

The product stream can include toluene, water, methanol or formaldehyde. The unconverted feedstocks can be separated from the product stream and then recycled to the one or more reactors. The process may include the step of passing the product stream to a separation stage for separating toluene, formaldehyde and methanol from the product stream. A stream containing toluene, formaldehyde and methanol may be obtained from the separation stage and recycled to the one or more reactors. The separation stage can include a membrane separation capable of removing hydrogen from the stream containing toluene, formaldehyde and methanol.

An aspect of the invention includes feeding toluene and formaldehyde to one or more reactors having a catalyst time on stream prior to regeneration of less than 1 hour. The toluene and formaldehyde are reacted in the one or more reactors to form a product stream including one or more of styrene, ethylbenzene, toluene, water, or formaldehyde. The product stream then passes to a separation stage for separating styrene and ethylbenzene from the second product stream. Methanol, toluene and formaldehyde, if present, can be separated from the product stream and recycled to the one or more reactors.

The one or more reactors can contain a reaction zone under reaction conditions containing a catalyst for reacting toluene and formaldehyde to form styrene. The one or more reactors can also include fluidized bed reactors. The fluidized bed reactors may include riser reactors, downer reactors, or a combination of both.

Another aspect of this invention relates to a process including introducing toluene into a fluidized bed reaction zone. The fluidized bed reaction zone may contain a top section, a bottom section, and an intermediate section, having a span that reaches between the top section and the bottom section. A C1 source is also introduced into the fluidized bed reaction zone, where it reacts with the toluene in the fluidized bed reaction zone to produce styrene and ethylbenzene. According to aspects of the invention, the toluene and C1 source have short contact times with the catalyst(s) in the reaction zone(s), for example having a catalyst time on stream prior to regeneration of less than 1 hour. The product including styrene and ethylbenzene is then recovered from the fluidized bed reaction zone. In an aspect, formaldehyde is independently fed to the reactor in addition to the C1 source and the toluene feed. In a further aspect, the C1 source includes formaldehyde.

The toluene feed may be injected at any point along the fluidized bed. The C1 source, which may include formaldehyde, may also be injected at any point along the fluidized bed. In an aspect, the toluene feed is injected downstream from C1 source injection point. In another aspect, the C1 source is injected downstream from the toluene feed injection point. In a further embodiment, both the C1 source and the toluene feed are injected at the same point along the fluidized bed.

DETAILED DESCRIPTION

In an aspect of the current invention, toluene is reacted with a carbon source, which can be referred to as a C1 source, over a catalyst in one or more reactors to produce styrene and ethylbenzene where the catalyst time on stream prior to regeneration is less than 1 hour. In an embodiment, the C1 source includes methanol or formaldehyde or a mixture of the two. In an alternative embodiment, toluene is reacted with one or more of the following: Formalin, Trioxane, Methylformcel, Paraformaldehyde and Methylal. In a further embodiment, the C1 source is selected from the group consisting of methanol, formaldehyde, Formalin (37-50% $H_2CO$ in solution of water and MeOH), Trioxane (1,3,5-trioxane), Methylformcel (55% $H_2CO$ in methanol), Paraformaldehyde and Methylal (dimethoxymethane), and combinations thereof.

Formaldehyde can be produced either by the oxidation or dehydrogenation of methanol. In an embodiment, formaldehyde is produced by the dehydrogenation of methanol to produce formaldehyde and hydrogen gas. This reaction step produces a dry formaldehyde stream that may be preferred, as it would not require the separation of the water prior to the reaction of the formaldehyde with toluene. Formaldehyde can also be produced by the oxidation of methanol to produce formaldehyde and water.

In the case of using a separate process to obtain formaldehyde, a separation unit may then be used in order to separate the formaldehyde from the hydrogen gas or water from the formaldehyde and unreacted methanol prior to reacting the formaldehyde with toluene for the production of styrene. This separation would inhibit the hydrogenation of the formaldehyde back to methanol. Purified formaldehyde could then be sent to styrene reactor and the unreacted methanol could be recycled.

Although the reaction has a 1:1 molar ratio of toluene and the C1 source, the ratio of the feedstreams is not limited within the present invention and can vary depending on operating conditions and the efficiency of the reaction system. If excess toluene or C1 source is fed to the reaction zone, the unreacted portion can be subsequently separated and recycled back into the process. In one embodiment the ratio of toluene:C1 source can range from between 100:1 to 1:100. In alternate embodiments the ratio of toluene:C1 source can range between from 50:1 to 1:50; from 20:1 to 1:20; from 10:1 to 1:10; from 5:1 to 1:5; from 2:1 to 1:2.

Figure 1:
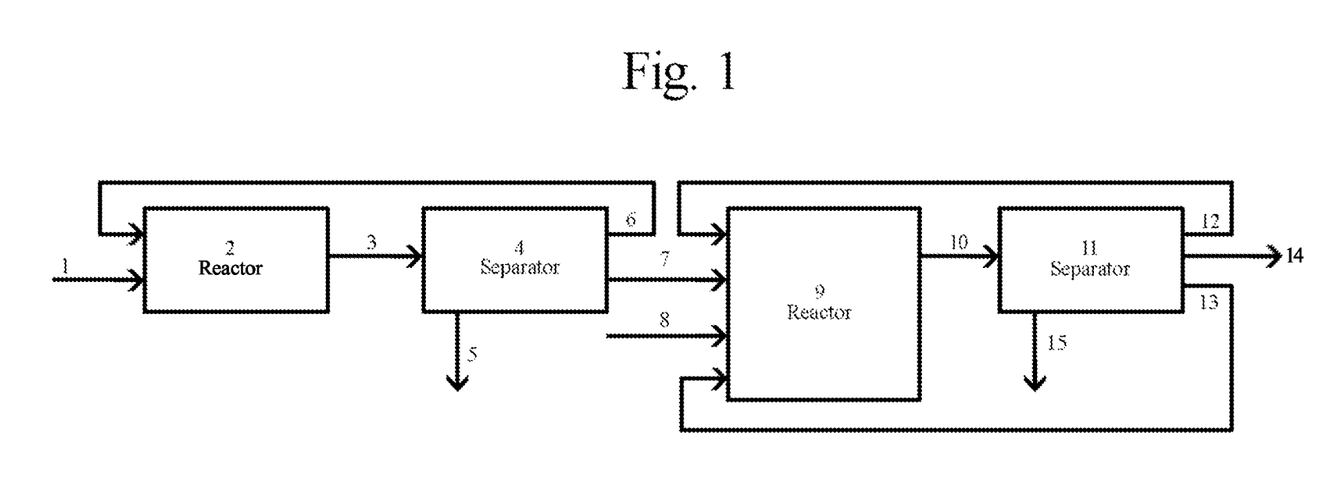
FIG. 1 illustrates a flow chart for the production of styrene by the reaction of formaldehyde and toluene, wherein the formaldehyde is first produced in a separate reactor by either the dehydrogenation or oxidation of methanol and is then reacted with toluene to produce styrene.

In FIG. 1 there is a simplified flow chart of one embodiment of the styrene production process described above. In this embodiment, a first reactor (2) is either a dehydrogenation reactor or an oxidation reactor. This reactor is designed to convert the first methanol feed (1) into formaldehyde. The gas product (3) of the reactor is then sent to a gas separation unit (4) where the formaldehyde is separated from any unreacted methanol and unwanted byproducts. Any unreacted methanol (6) can then be recycled back into the first reactor (2). The byproducts (5) are separated from the clean formaldehyde (7).

In one embodiment the first reactor (2) is a dehydrogenation reactor that produces formaldehyde and hydrogen and the separation unit (4) is a membrane capable of removing hydrogen from the product stream (3).

In an alternate embodiment the first reactor (2) is an oxidative reactor that produces product stream (3) including formaldehyde and water. The product stream (3) including formaldehyde and water can then be sent to the second reactor (9) without a separation unit (4).

The formaldehyde feed stream (7) is then reacted with a feed stream of toluene (8) in a second reactor (9). The toluene and formaldehyde react to produce styrene. The product (10) of the second reactor (9) may then be sent to an optional separation unit (11) where any unwanted byproducts (15) such as water can be separated from the styrene, unreacted formaldehyde and unreacted toluene. Any unreacted formaldehyde (12) and the unreacted toluene (13) can be recycled back into the reactor (9). A styrene product stream (14) can be removed from the separation unit (11) and subjected to further treatment or processing if desired.

The operating conditions of the reactors and separators can be system specific and can vary depending on the feedstream composition and the composition of the product streams. The reactor (9) for the reaction of toluene and formaldehyde will operate at elevated temperatures and pressures and may contain a basic or neutral catalyst system. The temperature can range in a non-limiting example from 250° C. to 750° C., optionally from 300° C. to 500° C., optionally from 325° C. to 450° C. The pressure can range in a non-limiting example from 1 atm to 70 atm, optionally from 1 atm to 35 atm, optionally from 1 atm to 5 atm.

Figure 2:
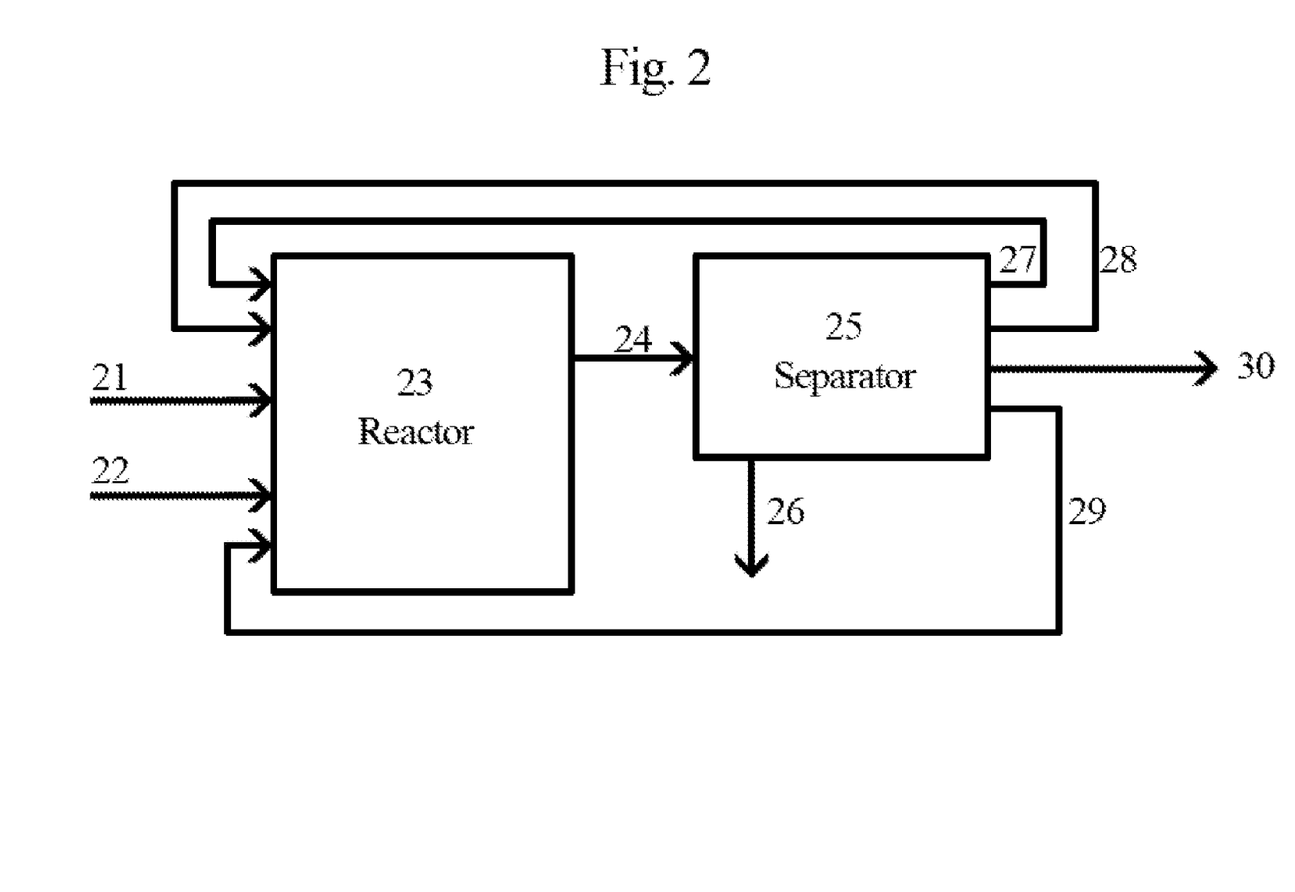
FIG. 2 illustrates a flow chart for the production of styrene by the reaction of formaldehyde and toluene, wherein methanol and toluene are fed into a reactor, wherein the methanol is converted to formaldehyde and the formaldehyde is reacted with toluene to produce styrene.

FIG. 2 is a simplified flow chart of another embodiment of the styrene process discussed above. A methanol containing feed stream (21) is fed along with a feed stream of toluene (22) in a reactor (23). The methanol reacts with a catalyst in the reactor to produce formaldehyde. The toluene and formaldehyde then react to produce styrene. The product (24) of the reactor (23) may then be sent to an optional separation unit (25) where any unwanted byproducts (26) can separated from the styrene, unreacted methanol, unreacted formaldehyde and unreacted toluene. Any unreacted methanol (27), unreacted formaldehyde (28) and the unreacted toluene (29) can be recycled back into the reactor (23). A styrene product stream (30) can be removed from the separation unit (25) and subjected to further treatment or processing if desired.

The operating conditions of the reactors and separators will be system specific and can vary depending on the feedstream composition and the composition of the product streams. The reactor (23) for the reactions of methanol to formaldehyde and toluene with formaldehyde will operate at elevated temperatures and pressures, such as for a non-limiting example from 250° C. to 750° C., optionally from 300° C. to 500° C., optionally from 325° C. to 450° C. The pressure can range from 1 atm to 70 atm, optionally from 1 atm to 35 atm, optionally from 1 atm to 5 atm and may contain an acidic, basic or neutral catalyst system.

Inert diluents such as helium and nitrogen may be included in the feed to adjust the gas partial pressures. Optionally, $CO_2$ or water (steam) can be included in the feed stream as these components may have beneficial properties, such as in the prevention of coke deposits. The reaction pressure is not a limiting factor regarding the present invention and any suitable condition is considered to be within the scope of the invention.

In the coupling reaction of toluene with a C1 source such as formaldehyde, the conversion of toluene has been observed to be highest at the earliest segment of the contact time between the fresh or regenerated catalyst and the reactants. The fresh or regenerated catalyst usage during the initial catalyst time on stream improves the conversion of toluene relative to that when the catalyst has been on stream for longer periods of time. In an aspect, the catalyst time on stream prior to catalyst regeneration is less than 1 hour. In optional embodiments the catalyst time on stream prior to regeneration is less than 30 seconds, less than 20 minutes, less than 10 minutes, less than 5 minutes, less than 1 minute, or less than 30 seconds.

Any suitable space velocity, within the short reaction time parameters of the present invention, can be considered to be within the scope of the invention. As used herein the space velocity shall be defined as: space velocity=[feed flow as vapor $(cm^3/h)$]/[catalyst weight (g)]. A standard reference temperature and pressure (72° F. and 14.7 psia) is used to convert a liquid under these conditions, such as toluene, to a feed vapor flow. For example: 0.076 $cm^3$/min of liquid toluene is converted into moles and then using 22.4 L/mol (as if it were an ideal gas) it is converted into a vapor flow of 16 $cm^3$/min. The space velocity can generally range from 15,000 $cm^3 g^{-1} h^{-1}$ to 100,000 $cm^3 g^{-1} h^{-1}$ optionally from 20,000 $cm^3 g^{-1} h^{-1}$ to 85,000 $cm^3 g^{-1} h^{-1}$. This range is an indication of possible space velocities, such as for a fixed bed reactor. Of course altering the catalyst composition, the amount of inert material, etc can alter the space velocity outside of this range. Also a change in the reactor from a fixed bed to an alternate design, such as a fluidized bed can also dramatically change the relative space velocity and can be outside of the stated range above. The space velocity ranges given are not limiting on the present invention and any suitable condition is considered to be within the scope of the invention.

In one embodiment the contact time is limited and the catalyst is continually being regenerated to enable the reaction to achieve a higher toluene conversion. In one embodiment a fluidized-bed reactor type of design is utilized to enable a short contact time and period of use of the catalyst prior to regeneration and to allow for a regeneration step to take place in order to bring the catalyst back to a more active state for reuse in the reactor in a recycle mode configuration.

Modification of the physical character of the catalyst to enhance the diffusion rate of the reactants to active sites and the products away from active sites would be advantageous to the conversion of reactants and selectivity of desired products. Another means of improvement of side chain alkylation selectivity can be to inhibit overly basic sites, such as for example with the addition of a boron compound. Such catalyst modifications include depositing the active components onto an inert substrate, optimizing the size of catalyst particles, and imparting void areas throughout the catalyst. Increasing porosity and/or increasing the surface area of the catalyst can accomplish this optimization.

Improvement in side chain alkylation selectivity may be achieved by treating a molecular sieve zeolite catalyst with proper chemical compounds to inhibit the external acidic sites and minimize aromatic alkylation on the ring positions. Another means of improvement of side chain alkylation selectivity can be to impose restrictions on the catalyst structure to facilitate side chain alkylation. In an embodiment the catalyst used in an embodiment of the present invention is an acidic, basic or neutral catalyst. In an embodiment the catalyst has predominately basic characteristics but can still contain weakly acidic sites.

The catalytic reaction systems suitable for this invention can include one or more of the zeolite or amorphous materials modified for side chain alkylation selectivity. A non-limiting example can be a zeolite promoted with one or more of the following: Ru, Rh, Ni, Co, Pd, Pt, Mn, Ti, Zr, V, Nb, K, Cs, Ga, B, P, Rb or Na. In an embodiment, the zeolite can be promoted with one or more of Cs, B, Co, or Ga.

Zeolite materials suitable for this invention may include aluminosilicate-based zeolites and amorphous compounds such as faujasites, mordenites, etc. Silicate-based zeolites are made of alternating $SiO_2$ and $MO_x$ tetrahedral, where M is an element selected from the Groups 1 through 16 of the Periodic Table (new IUPAC). These types of zeolites have 4-, 6-, 8-, 10-, or 12-membered oxygen ring channels. An example of zeolites of this invention can include faujasites. Other suitable zeolite materials include X-type and Y-type zeolites. In a more specific embodiment, the zeolite is an X-type zeolite.

A catalyst comprising a substrate, such as a zeolite or faujasite, that supports a promoting metal or a combination of metals can be used to catalyze the reaction of hydrocarbons. The method of preparing the catalyst, pretreatment of the catalyst, and reaction conditions can influence the conversion, selectivity, and yield of the reactions.

The various elements that make up the catalyst can be derived from any suitable source, such as in their elemental form, or in compounds or coordination complexes of an organic or inorganic nature, such as carbonates, oxides, hydroxides, nitrates, acetates, chlorides, phosphates, sulfides and sulfonates. The elements and/or compounds can be prepared by any suitable method, known in the art, for the preparation of such materials.

The term "substrate" as used herein is not meant to indicate that this component is necessarily inactive, while the other metals and/or promoters are the active species. On the contrary, the substrate can be an active part of the catalyst. The term "substrate" would merely imply that the substrate makes up a significant quantity, generally 10% or more by weight, of the entire catalyst. The promoters individually can range from 0.01% to 60% by weight of the catalyst, optionally from 0.01% to 50%. If more than one promoters are combined, they together generally can range from 0.01% up to 70% by weight of the catalyst. The elements of the catalyst composition can be provided from any suitable source, such as in its elemental form, as a salt, as a coordination compound, etc.

The addition of a support material to improve the catalyst physical properties is possible within the present invention. Binder material, extrusion aids or other additives can be added to the catalyst composition or the final catalyst composition can be added to a structured material that provides a support structure. For example, the final catalyst composition can include an alumina or aluminate framework as a support. Upon calcination these elements can be altered, such as through oxidation which would increase the relative content of oxygen within the final catalyst structure. The combination of the catalyst of the present invention combined with additional elements such as a binder, extrusion aid, structured material, or other additives, and their respective calcination products, are included within the scope of the invention.

In one embodiment, the catalyst can be prepared by combining a substrate with at least one promoter element. Embodiments of a substrate can be a molecular sieve, from either natural or synthetic sources. Zeolites and zeolite-like materials can be an effective substrate. Alternate molecular sieves also contemplated are zeolite-like materials the crystalline silicoaluminophosphates (SAPO) and the aluminophosphates (ALPO).

The present invention is not limited by the method of catalyst preparation, and all suitable methods should be considered to fall within the scope herein. Particularly effective techniques are those utilized for the preparation of solid catalysts. Conventional methods include co-precipitation from an aqueous, an organic or a combination solution-dispersion, impregnation, dry mixing, wet mixing or the like, alone or in various combinations. In general, any method can be used which provides compositions of matter containing the prescribed components in effective amounts. According to an embodiment the substrate is charged with promoter via an incipient wetness impregnation. Other impregnation techniques such as by soaking, pore volume impregnation, or percolation can optionally be used. Alternate methods such as ion exchange, wash coat, precipitation, and gel formation can also be used. Various methods and procedures for catalyst preparation are listed in the technical report Manual of Methods and Procedures for Catalyst Characterization by J. Haber, J. H. Block and B. Dolmon, published in the International Union of Pure and Applied Chemistry, Volume 67, Nos 8/9, pp. 1257-1306, 1995, incorporated herein in its entirety.

When slurries, precipitates or the like are prepared, they will generally be dried, usually at a temperature sufficient to volatilize the water or other carrier, such as from 100° C. to 250° C., with or without vacuum. Irrespective of how the components are combined and irrespective of the source of the components, the dried composition is generally calcined in the presence of a free oxygen-containing gas, usually at temperatures between about 300° C. and about 900° C. for from 1 to 24 hours. The calcination can be in an oxygen-containing atmosphere, or alternately in a reducing or inert atmosphere.

The prepared catalyst can be ground, pressed, sieved, shaped and/or otherwise processed into a form suitable for loading into a reactor. The reactor can be any type known in the art to make catalyst particles, such as a fixed bed, fluidized bed, or swing bed reactor. Optionally an inert material, such as quartz chips, can be used to support the catalyst bed and to place the catalyst within the bed. Depending on the catalyst, a pretreatment of the catalyst may, or may not, be necessary. For the pretreatment, the reactor can be heated to elevated temperatures, such as 200° C. to 900° C. with an air flow, such as 100 mL/min, and held at these conditions for a length of time, such as 1 to 3 hours. Then, the reactor can be brought to the operating temperature of the reactor, for example 300° C. to 550° C., or optionally down to atmospheric or other desired temperature. The reactor can be kept under an inert purge, such as under a nitrogen or helium purge.

The present catalyst is adaptable to use in the various physical forms in which catalysts are commonly used. The catalyst of the invention may be used as a particulate material in a contact bed or as a coating material on structures having a high surface area. If desired, the catalyst can be deposited with various catalyst binder and/or support materials, which do not adversely affect the catalyst or the reactions in which the catalyst is to be employed.

Embodiments of reactors that can be used with the present invention can include, by non-limiting examples: fluid bed reactors, fixed bed reactors, and entrained bed reactors. In one embodiment multiple fixed bed reactors are used as swing beds wherein some beds are on line while other beds are taken out of service and are being regenerated.

Reactors capable of the elevated temperature and pressure as described herein, and capable of enabling contact of the reactants with the catalyst, can be considered within the scope of the present invention. Embodiments of the particular reactor system may be determined based on the particular design conditions and throughput, as by one of ordinary skill in the art, and are not meant to be limiting on the scope of the present invention.

Figure 3:
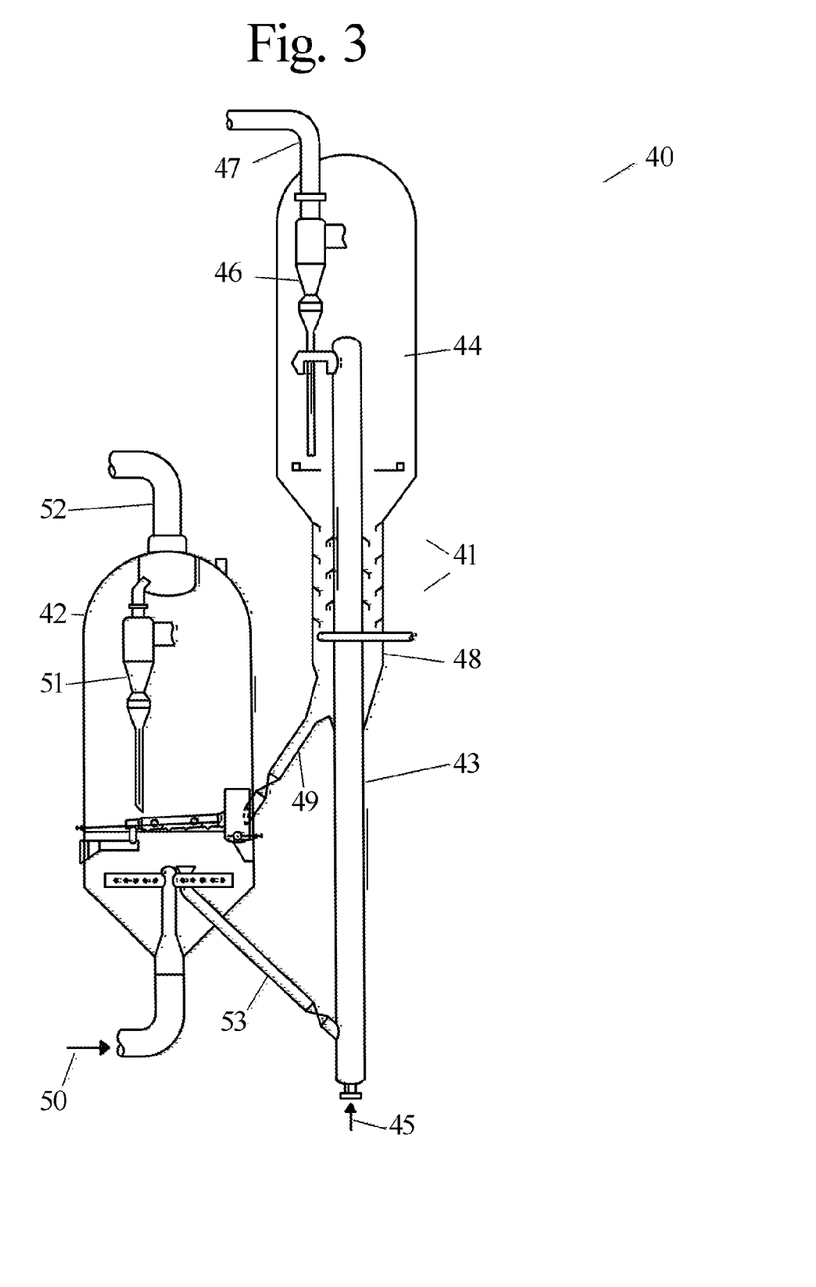
FIG. 3 is a schematic illustration of an aspect of an embodiment of the present invention having the capability for continuous reaction with catalyst regeneration.

An example of a fluid bed reactor having catalyst regeneration capabilities that may be employed with the present invention is illustrated in FIG. 3. This type of reactor system employing a riser can be modified as needed, for example by insulating or heating the riser if thermal input is needed, or by jacketing the riser with cooling water if thermal dissipation is required. These designs can also be used to replace catalyst while the process is in operation, by withdrawing catalyst from the regeneration vessel from an exit line (not shown) or adding new catalyst into the system while in operation. The riser reactor can be replaced with a downer reactor (not shown). In an embodiment (not shown), the reaction zone includes both riser and downer reactors.

FIG. 3 is a schematic illustration of an aspect of an embodiment of the present invention having the capability for continuous reaction with catalyst regeneration. The reaction process (40) generally includes two main zones for reaction (41) and regeneration (42). A reaction zone can include a vertical conduit, or riser (43), as the main reaction site, with the effluent of the conduit emptying into a large volume process vessel, which may be referred to as a separation vessel (44). In the reaction riser (43), a feed stream (45), such as toluene and methanol, is contacted with a fluidized catalyst, which can be a relatively large fluidized bed of catalyst, at reactor conditions. The residence time of catalyst and hydrocarbons in the riser (43) needed for substantial completion of the reaction may vary as needed for the specific reactor design and throughput design. The flowing vapor/catalyst stream leaving the riser (43) may pass from the riser to a solids-vapor separation device, such as a cyclone (46), normally located within and at the top of the separation vessel (44). The products of the reaction can be separated from the portion of catalyst that is carried by the vapor stream by means of one or more cyclone (46) and the products can exit the cyclone (46) and separation vessel (44) via line (47). The spent catalyst falls downward to a stripper (48) located in a lower part of the separation vessel (44). Catalyst can be transferred to a regeneration vessel (42) by way of a conduit (49) connected to the stripper (48).

The catalyst can be continuously circulated from the reaction zone (41) to the regeneration vessel (42) and then again to the reaction zone (41). The catalyst can therefore act as a vehicle for the transfer of heat from zone to zone as well as providing the necessary catalytic activity. Catalyst from the reaction zone (41) that is being transferred to the regeneration zone (42) can be referred to as "spent catalyst". The term "spent catalyst" is not intended to be indicative of a total lack of catalytic activity by the catalyst particles. Catalyst, which is being withdrawn from the regeneration vessel (42), is referred to as "regenerated" catalyst. The catalyst can be regenerated in the regeneration vessel (42) by heat and contact with a regeneration stream (50). The regeneration stream (50) can include oxygen, hydrogen, steam and combinations thereof. The regenerated catalyst can be separated from the regeneration stream by the use of one or more cyclones (51) that can enable the removal of the regeneration vessel (42) via line (52). The regenerated catalyst can be transferred via line (53) to the lower section of the riser (43) where it is again in contact with the feed stream (45) and can flow up the riser (43).

In an aspect, the reactants may be injected into the reactor(s) in a stage-wise manner. The fluidized bed reaction zone may contain a top section, a bottom section, and an intermediate section, having a span that reaches between the top section and the bottom section. The toluene feed may be injected at any point, or points, along the fluidized bed. The C1 source, which may include formaldehyde, may also be injected at any point, or points, along the fluidized bed. In an aspect, the toluene feed is injected downstream from C1 source injection point. In another aspect, the C1 source is injected downstream from the toluene feed injection point. In a further embodiment, both the C1 source and the toluene feed are injected at the same point along the fluidized bed. In an aspect, the fluidized bed is a dense bed fluidized reactor.

The toluene and formaldehyde coupling reaction may have a toluene conversion percent greater than about 0.01-wt %. In an embodiment the toluene and formaldehyde coupling reaction is capable of having a toluene conversion percent in the range of from about 0.05-wt % to about 5-wt %. In a further embodiment the toluene and formaldehyde coupling reaction is capable of having a toluene conversion in the range of from about 2-wt % to about 4-wt %.

In an aspect the toluene and formaldehyde coupling reaction is capable of selectivity to styrene greater up to about 85-wt %. In another aspect, the toluene and formaldehyde coupling reaction is capable of selectivity to styrene in the range of from about 60-wt % to about 80-wt %. In an aspect the toluene to formaldehyde coupling reaction is capable of selectivity to ethylbenzene in the range of from about 10-wt % to about 50-wt %. In another aspect, the toluene to formaldehyde coupling reaction is capable of selectivity to ethylbenzene in the range of from about 15-wt % to about 35%. In an embodiment, the ratio of selectivity to styrene and selectivity to ethylbenzene ($S_{sty}:S_{EB}$) is in the range of from about 5:1 to about 5:3.

Products leaving the reactor can be monitored with gas chromatography, or by some other method. Products can be separated using distillation or some other method.

EXAMPLE

Experiments were carried out with formalin (37 wt % formaldehyde, 15 wt % methanol, and 48 wt % water) and toluene over an X-type zeolite catalyst containing boron and cesium. A 0.75-inch outside diameter stainless steel tube was fitted with a 0.5-inch inside diameter ceramic liner. The tube was then filled with crushed quartz (to a height of about 13.5-inches), then filled with 10.2 grams (12.0 cc) of the catalyst, and then more crushed quartz is added to bring the quartz/catalyst/quartz bed to a height of about 17-inches. A pyropaint-coated thermowell was positioned in the middle of the bed. The reactor was installed in a 3-zone furnace and heated to 500° C. and held for 2 hours while passing nitrogen through it at 150 cc/min. The reactor was then cooled to the reaction temperature of 375° C. The feed was toluene, formalin, and nitrogen. The inlet flow rates were not corrected for temperature. The effluent was monitored by an on-line gas chromatograph.

The cesium ion-exchanged zeolite material was made by the following procedure: A glass cylinder (2" inside diameter), fitted with a sintered glass disk and stopcock at the lower end, was charged with 544-HP zeolite (100 g, W. C. Grace) and CsOH (400 mL, 1.0 M in water). The mixture was then brought to 90° C. and allowed to stand for 4 h. The liquid was drained from the zeolite material and another aliquot of CsOH (400 mL of 1.0 M solution in water) was added and allowed to stand for 3 hours at 90° C. The liquid was drained from the zeolite material and another aliquot of CsOH (400 mL of 1.0 M solution in water) was added and allowed to stand for 15 hours at 90° C. The liquid was drained from the zeolite material and dried at 150° C. for 1.5 hours.

Deposition of 0.3 wt % boron onto cesium ion-exchanged zeolite material: The cesium ion-exchanged zeolite material (100 g) was treated with a solution of boric acid (1.52 g) dissolved in acetone (500 mL) at room temperature for 2 hours. The (Cs,B)/X material was then dried at 150° C. for 12 hours. This catalyst was used for the example shown in Table 1.

The information in Table 1 describes the results of the above reaction in producing styrene and ethylbenzene from toluene and formalin. It is seen that styrene selectivity decreases during the run and that the highest toluene conversion is at the beginning of the test and at a short contact time. A short contact time and fresh catalyst is seen to result in the highest toluene conversion. The first conversion reading was taken 20 minutes after the start of the run and the toluene conversion was 3.7 wt %. The second conversion reading was taken 57 minutes into the run and the toluene conversion dropped to 1.9 wt %. Increasing the contact time during the test improved the toluene conversion but did not bring it to the conversion level at the beginning of the run. Zero selectivity to o-xylene, cumene, phenylacetylene, 1,2,4-trimethylbenzene, and benzaldehyde was observed. The toluene conversion versus contact times from Table 1 is graphed in FIG. 4. The toluene conversion versus on stream time from Table 1 is graphed in FIG. 5.

TABLE 1

| | | Time | | | | | |
|---|---|---|---|---|---|---|---|
| | | 8:15 | 8:35 | 9:12 | 10:10 | 10:50 | 11:30 | 12:30 |
| | | On Stream Time, min | | | | | |
| | | 20 | 57 | 115 | 155 | 195 | 255 |
| WHSV | Total Flow, (weight of feed g/hr/weight of catalyst g) | 5.70 | 5.70 | 2.06 | 2.06 | 0.75 | 0.75 |
| Contact Time, sec | 1/GSHV*3600 sec | 0.71 | 0.70 | 1.6 | 1.7 | 3.9 | 4.1 |
| Toluene Conversion | | 3.7 | 1.9 | 1.6 | 1.5 | 2.7 | 2.1 |
| Selectivity | benzene | 0.5 | 0.5 | 0.6 | 0.6 | 0.7 | 1.0 |
| | ethylbenzene | 20.4 | 19.1 | 20.5 | 21.4 | 33.0 | 27.9 |
| | p-xylene + m-xylene + o-xylene | 0.3 | 0.5 | 0.6 | 0.6 | 3.7 | 0.5 |
| | styrene | 71.5 | 71.3 | 73.1 | 72.7 | 61.9 | 67.8 |
| | 1-alpha-methylstyrene | 6.7 | 8.0 | 4.5 | 4.5 | 2.9 | 1.9 |

Figure 4:
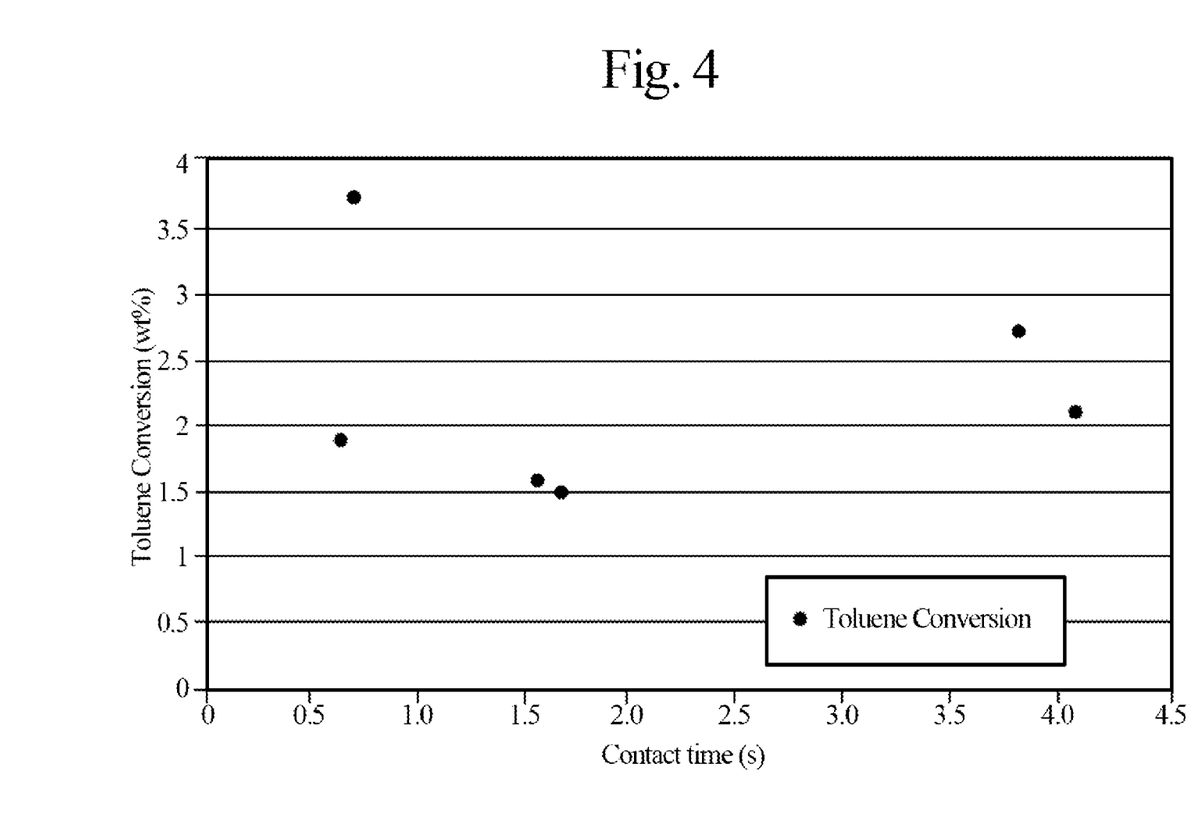
FIG. 4 is a graph of toluene conversion versus contact times in an example of the present invention.

Referring to FIG. 4, the highest conversion of toluene (3.7 mol %) is at a contact time of 0.71 seconds and at the start of the test when the catalyst is fresh and has not had the deleterious deactivation effects from an extended run time. The other data points show a lower rate of conversion of toluene at both shorter and longer contact times.

Figure 5:
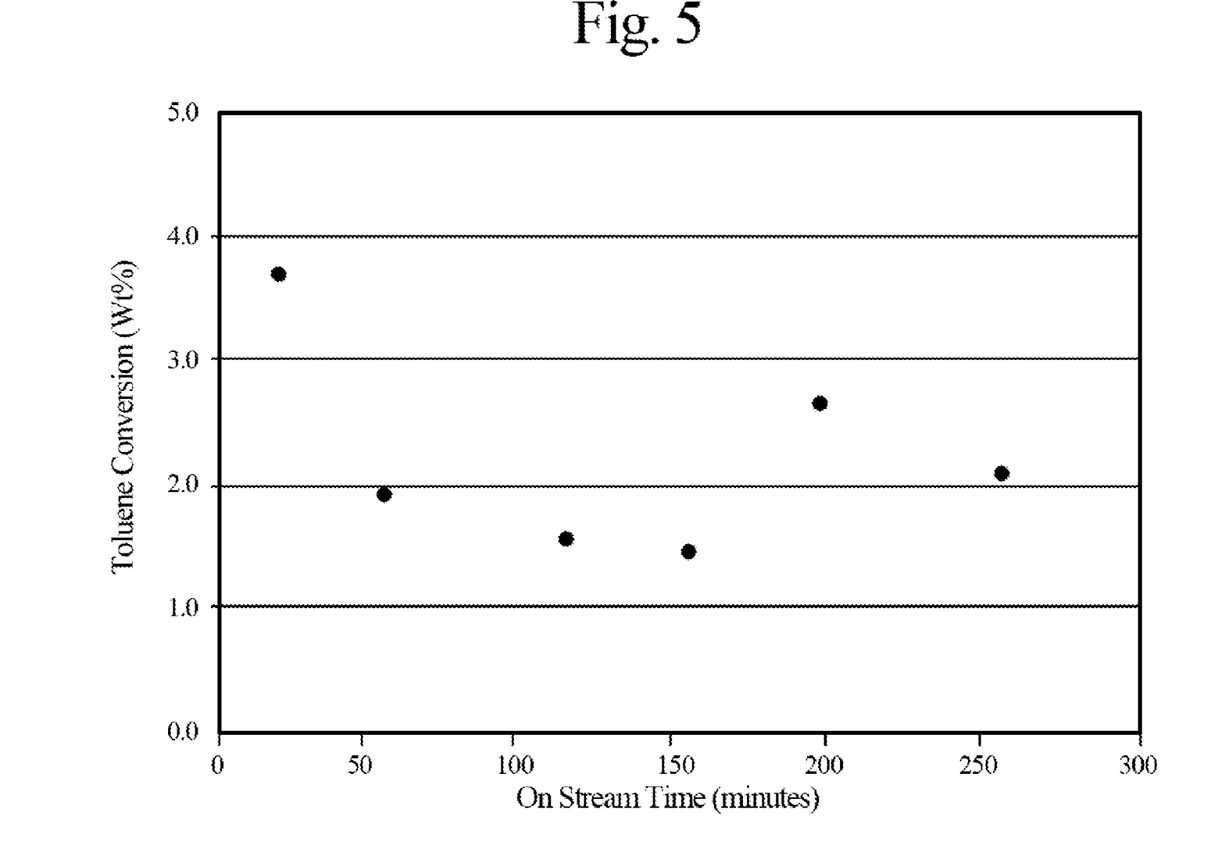
FIG. 5 is a graph of the toluene conversion versus on stream time in an example of the present invention.

Referring to FIG. 5, the highest conversion of toluene is at an on stream time of 20 minutes while the catalyst is fresh and has not had the deleterious deactivation effects from an extended run time. The other data points show a lower rate of conversion as the time on stream increases, indicating a benefit to having a restricted time on stream for the catalyst.

The term "conversion" refers to the percentage of reactant (e.g. toluene) that undergoes a chemical reaction.

$X_{Tol}$=conversion of toluene (mol %)=$(Tol_{in}-Tol_{out})/Tol_{in}$ $X_{MeOH}$=conversion of methanol to styrene+ethylbenzene (mol %)

The term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

The term "regenerated catalyst" refers to a catalyst that has regained enough activity to be efficient in a specified process. Such efficiency is determined by individual process parameters.

The term "selectivity" refers to the relative activity of a catalyst in reference to a particular compound in a mixture. Selectivity is quantified as the proportion of a particular product relative to all other products.

$S_{Sty}$=selectivity of toluene to styrene (mol %)=$Sty_{out}/Tol_{converted}$ $S_{Bz}$=selectivity of toluene to benzene (mol %)=$Benzene_{out}/Tol_{converted}$ $S_{EB}$=selectivity of toluene to ethylbenzene (mol %)=$EB_{out}/Tol_{converted}$ $S_{Xyl}$=selectivity of toluene to xylenes (mol %)=$Xylenes_{out}/Tol_{converted}$ $S_{Sty+EB}$ (MeOH)=selectivity of methanol to styrene+ethylbenzene (mol %)=$(Sty_{out}+EB_{out})/MeOH_{converted}$ The term "spent catalyst" refers to a catalyst that has lost enough catalyst activity to no longer be efficient in a specified process. Such efficiency is determined by individual process parameters.

The term "zeolite" refers to a molecular sieve containing a silicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves. An X-zeolite is defined as having a Si/Al molar ratio between 1.0 and 1.7. A Y-zeolite is defined as having a Si/Al molar ratio greater than 1.7.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

What is claimed is:

1. A process for making styrene comprising:
    converting at least a portion of a C1 source containing a mixture of methanol and formaldehyde to formaldehyde in one or more fluidized bed reactors containing a catalyst comprising a X-type zeolite, boron, and cesium;
    reacting toluene with the formaldehyde in the one or more reactors to form a product stream comprising styrene and ethylbenzene;
    withdrawing the product stream and spent catalyst from the one or more fluidized reactors;

regenerating the spent catalyst in a catalyst regeneration zone to produce regenerated catalyst; and recycling the regenerated catalyst to the one or more reactors; and wherein catalyst time on stream prior to regeneration is less than 30 minutes.

2. The process of claim 1, wherein the one or more reactors comprises a reaction zone under reaction conditions containing a catalyst for reacting toluene and formaldehyde to form styrene and for converting methanol to formaldehyde.

3. The process of claim 1, wherein toluene conversion is greater than 1 wt %.

4. The process of claim 2, wherein selectivity to styrene is greater than 30 wt % and selectivity to ethylbenzene is greater than 15 wt %.

5. The process of claim 1, wherein the toluene and C1 source are each injected at multiple points along the fluidized bed.

* * * * *